US006248513B1

(12) United States Patent
Horaud et al.

(10) Patent No.: US 6,248,513 B1
(45) Date of Patent: Jun. 19, 2001

(54) ANTICYTOMEGALOVIRUS MONOCLONAL ANTIBODIES AND PROCESSES FOR THE IN VITRO DIAGNOSIS OF INFECTIONS BY HUMAN CYTOMEGALOVIRUSES AND A PROTEIN-KINASE INDUCIBLE BY CYTOMEGALOVIRUSES AND RECOGNIZABLE BY AFORESAID MONOCLONAL ANTIBODIES

(75) Inventors: Florian Horaud, Meudon; Susan Michelson, Noisy le Roi; Octavian Barzu, Massy; Andre Boue, Saint-Cyr l'Ecole; Claire Amadei, Courbevoie, all of (FR)

(73) Assignees: Institut Pasteur; Centre National de la Recherchie Scientifique; Institut National de la Sante/de la Recherche Medicale, all of Paris (FR)

( * ) Notice: Subject to any disclaimer, the term of this patent is extended or adjusted under 35 U.S.C. 154(b) by 0 days.

(21) Appl. No.: 08/488,416

(22) Filed: Jun. 7, 1995

Related U.S. Application Data

(63) Continuation of application No. 06/727,533, filed on Apr. 26, 1985, now abandoned.

(30) Foreign Application Priority Data

Apr. 27, 1984 (FR) .................................. 84 06769

(51) Int. Cl.$^7$ .............................. C12Q 1/70; C07K 16/08
(52) U.S. Cl. ............................................ 435/5; 530/388.1
(58) Field of Search ................................ 424/130, 140.1, 424/147.1, 146.1, 152.1, 204.1, 231.1; 435/5, 7.1, 7.4, 15; 530/352, 360, 388.3, 388.15, 403, 388.1; 436/501, 546, 548, 518, 811

(56) References Cited

PUBLICATIONS

Michelson, European Symposium on New Horizons in Microbiology, A. Sanna and G. Morace eds., Elsevier Science Publishers B.V., 149–156, 1984.*
Michelson et al., Virology, 134:259–268, 1984.*
Amadei et al., Ann. Virol. (Inst. Pasteur) 134, No. 2, 165–180, 1983.*
Mar et al., J. Gen. Virol., 57:149–156, 1981.*
Stinski et al., J. Virol., vol. 26, No. 3:686–701, Jun 1978.*
Britt, W.J. et al., J. Virol., 59:185–188, Jul. 1986.*
Pereira, L. et al., Infection and Immunity, vol. 36, No. 3:924–932, Jun. 1982.*

Li et al., "Production and Characterization of Monoclonal Antibodies against Cytomegalovirus Virions", p. 293, # S 52, Abstracts of the Annual Meeting of the American Society for Microbiology, Mar. 1983.*
Murayama et al. J. Gen. Virol. 67:1475–1478, 1986.*
Schmitz, H. et al., "Human Immune Response to Proteins of Cytomegalovirus", *Intervirology* 13:154–161 (1980).
Iêda Siqueira–Linhares, Maria et al., "Polypeptides and Major Antigens of Four New Isolates of Cytomegalovirus", *Medical Microbiology Immunology* 169:197–208 (1981).
Murayama et al., "Fc Receptors(s) Induced by Human Immunoglobulin G Subclasses", J. Gen. Virol., 67:1475–1478 (1986).
Lucas et al., "Rapid Diagnosis of Cytomegalovirus by Indirect Immunofluorescence Assay with Monoclonal Antibody F6b in a Commercially Available Kit", Journal of Clinical Microbiology, 27(2):367–369 (Feb. 1989).
Amadei et al, Ann. Virol., vol. 134, No. 2, pp. 165–180, 1983.*
Goldstein et al, Infection and Immunity, vol. 38, No. 1, p273–281, 1982.*
Pereira et al, Infection and Immunity, vol. 36, p. 924–932, 1982.*
Michelson, Elsevier Science Publishers B.V., New Horizons in Microbiology, A. Sanna and G. Morace Editors, 1984.*
Amadei et al, *Ann. Virol.*, vol. 134, No. 2, pp. 165–180 (1983).
Kim et al, *Journal of Clinical Microbiology*, vol. 18, No. 2, pp. 331–343 (1983).
Mar et al, *Chemical Abstracts*, vol. 96, No. 9, p. 237, 64720Z (1982).
Pereira et al, *Infection and Immunity*, vol. 36, pp. 924–932 (Jun. 1982).
Infection and Immunity, Oct. 1982, p. 273–281, vol. 38 Goldstein et al.*
Virology, vol. 134, p. 259–268 (1984), Michelson et al.*

* cited by examiner

Primary Examiner—Anthony C. Caputa
Assistant Examiner—Brenda G. Brumback
(74) Attorney, Agent, or Firm—Burns, Doane, Swecker & Mathis, L.L.P.

(57) ABSTRACT

The invention relates to a process for in vitro diagnosis of an infection by human cytomegaloviruses. The process consists of contacting cells possibly carrying the infection, with a monoclonal antibody reacting with a polypeptide of molecular weight 68,000, induced by human cytomegalovirus and which possesses a protein-kinase activity. The detection of the reaction is preferably carried out by immunofluorescence.

8 Claims, No Drawings

ANTICYTOMEGALOVIRUS MONOCLONAL ANTIBODIES AND PROCESSES FOR THE IN VITRO DIAGNOSIS OF INFECTIONS BY HUMAN CYTOMEGALOVIRUSES AND A PROTEIN-KINASE INDUCIBLE BY CYTOMEGALOVIRUSES AND RECOGNIZABLE BY AFORESAID MONOCLONAL ANTIBODIES

This application is a continuation of patent application Ser. No. 06/727,533, filed Apr. 26, 1985, now abandoned.

The invention relates to human anticytomegalovirus monoclonal antibodies (HCMV) and to a process for the in vitro diagnosis of infections induced by human cytomegaloviruses. It relates more particularly to antibodies of this type which are capable of simultaneously detecting human cytomegaloviruses (CMV), human cells infected by CMV and a polypeptide, particularly a protein induced by HCMV and having protein-kinase activity.

The invention relates also to the aforesaid polypeptide having the aforesaid protein-kinase activity.

It is known that CMV is the cause of numerous clinical infections, ranging between benign infectious manifestations, and congenital manifestations, for example, particularly severe malformations. CMV has also been recognised as a cause of morbidity and mortality in persons who have undergone organ transplants, for example, of the kidney. The detection of CMV is a problem which poses itself therefore particularly acutely. In addition, the recognition and isolation of vaccinating polypeptides or proteins, or which can be rendered vaccinating with respect to CMV would open up serious possibilities of prevention of said complications against which at the present time, few means of treatment are available.

Various authors have already brought their attention to bear on diagnosis techniques, which could be based on the use of monoclonal antibodies with respect to the human cytomegalovirus. The monoclonal antibodies obtained hitherto, did not yet contribute the expected solution for performing a diagnosis, which is both easy and reliable, of infection with cytomegamoviruses.

In fact, it is known that CMV (a member of the family of viruses of herpes) induces in the infected cells a considerable number of polypeptides, at various stages of the infectious process, and at various levels of the infected cells. L. N. PEREIRA and Coll. ("Infection and Immunity"), June 1982, p. 924–932, report, that they have produced a large number of hybridomas secretors of monoclonal antibodies, capable, of recognising in previously unfixed cells, polypeptides, or glycoproteins induced by the CMV in cultures of these cells. The differences observed by PEREIRA and Coll. at the level of the relative behaviour of different antibodies with respect to the virus itself, infected cells and proteins, glycoproteins, or polypeptides, isolatable from extracts of these cells, has led them to formulate the hypothesis, that the conformation of the viral glycoproteins recognised by certain of these antibodies at the membranal surface of the cells infected by the CMV's, could be different from the conformation of the envelope of the virion. The utilization of certain of the antibodies isolated to perform diagnosis operations of the above-indicated type, has been evoked by these authors. It follows however from the foregoing and from the experimental results provided, that the monoclonal antibodies judged the most interesting, were also capable of precipitating several polypeptides at the same time. The use of these antibodies to recognise antigenic determinants, or specific epitopes, could not therefore be contemplated by reason of the non-discriminating character of the recognition.

L. C. GOLDSTEIN and Coll. ("Infections and Immunity", October 1982, p. 273–281) also described a certain number of monoclonal antibodies which can recognise certain polypeptides localised in the nuclei, or in cytoplasmic inclusions of cells infected by CMV. These monoclonal antibodies have been selected by their capacity to react with cells infected by CMV, and previously fixed with absolute methanol and dried in air. It does not however follow from the article that these monoclonal antibodies were adapted to recognise still intact infected cells.

Lastly, C. AMEDEI and Coll. (Ann. Virol. (Institut Pasteur), describe a battery, of 24 monoclonal antibodies directed against human cytomegalovirus. The larger number of monoclonal antibodies obtained, arises apparently, from the techniques which have been used to detect them. In particular, detection has employed immunofluorescent techniques of detection of antibodies retained on previously infected cells, which had been fixed with acetone and dried in air. The same monoclonal antibodies are revealed to be practically devoid of activity with respect to cells obtained from identical cell lines, previously infected by the same virus, when these infected cells had been fixed beforehand with methanol. Perhaps there should be sought in this observation, the cause of the low number of hybridomas secreting monoclonal antibodies selective against cells infected with HCMV, which had been isolated by L. C GOLDSTEIN and Coll.

Among these monoclonal antibodies, some have been found to show neutralising properties with respect to several strains of virus. These monoclonal antibodies have moreover been the subject of a French Patent Application No. 83 05384, filed Mar. 31, 1983. These particular monoclonal antibodies have been adopted for the carrying out of in vitro diagnosis tests-of an infection with HCMV. However, the Patent Application and indeed, moreover, the above-mentioned article, have not recognised among the various hybridomas described, that which is established in the following to secrete monoclonal antibodies, particularly effective for diagnosis operations, and suitable to permit the isolation of a polypeptide inducible by HCMV's and endowed with biological properties permitting a particularly refined diagnosis operation.

It is an object of the invention to provide a method of diagnosis employing monoclonal antibodies resulting from a selection amongst all of those which have been described in the state of the art. The use of these selected antibodies in in vitro diagnosis tests, is both easy and accurate. They recognise a protein induced by HCMV's in still intact infected cells in immunofluorescence tests. These antibodies are capable of providing positive responses during almost the whole of the infectious cycle. The diagnosis can be improved and confirmed in dosage tests of the enzymatic activity. The infected cells produce polypeptides, proteins of glycoproteins, which are induced by the HCMV's. These polypeptides are moreover bearers of an epitope, or continuous sequential antigenic determinant. By the expression "bearer of an epitope or antigenic determinant", must be understood a determinant whose recognition by the antibodies is not connected with the particular conformation of this site on the natural polypeptides, proteins or glycoproteins of the virus, or induced by the latter in the cells that it infects.

The invention results from the discovery which the inventors have made, that the hybridoma secreting monoclonal antibodies previously described, complies with all of these, conditions. More particularly, the invention relates to the use of monoclonal antibodies produced by the secreting hybridomas concerned for the detection in vitro of a sequential antigenic determinant borne by a protein, of which the molecular weight is in the vicinity of 68,000, isolatable without degradation from extracts of cells infected by a CMV strain, this protein possessing in addition, protein-kinase properties.

In other words, the human anticytomegalovirus monoclonal antibody employed in the process according to the invention for the in vitro diagnosis of infections induced by human cytomegaloviruses and for the detection of a protein-kinase inducible by human cytomegaloviruses in human cells, and particularly in human cell lines, can be defined by the combination of its capacities:

- to give rise to reactions detectable by immunofluorescence, on culture cells of human origin, previously infected with HCMV and fixed with acetone
- to react with essentially a single viral polypeptide induced by HCMV's in cells of human origin previously infected by them, this polypeptide having a molecular weight of the order of 68,000, the bearer of a continuous sequential epitope, this polypeptide appearing in the nuclei and then diffusing, at least in part, into the cytoplasm of the said infected cells, from which it can be isolated,
- preferably, to be fixed on protein A.

The invention relates, still more particularly, within the scope of the above said applications, to monoclonal antibodies which recognise a polypeptide responding to the following characteristics.

It appears precociously in the cell (it is detectable 3 to 5 hours after the adsorption of the virus on the cell);

it is specific to human CMV;

it is accumulated in the cells infected by CMV;

it persists at least 4 days in the cells from the moment of its appearance (and this particularly in human fibroblasts of the MRC5 lung type); it possesses all of the properties of the preferred polypeptides, whose characteristics are indicated below.

The preferred monoclonal antibodies are those which do not react with non-specific receptors of IgG, and more particularly still, those which are characterised by their capacity to detect the above-said polypeptide in cells infected by any HCMV, whatever the origin thereof, for example, strains known under the name Ad-169, Towne & Davis. A preferred monoclonal antibody is that which is produced by the hybridoma deposited in the National Collection of Micro-Organisms and Cultures (C.N.C.M), under No. I-289 on Mar. 27, 1984.

The above said monoclonal antibodies are obtained by a process employing hybridomas secreting monoclonal antibodies neutralising the HCMV viruses previously formed between cells of myelomas and spleen cells of an animal previously immunised against a HCMV, such as the strain HDIV Ad-169, this process being more particularly characterised in that;

the said neutralising antibodies are made to react with human cells in cultures previously infected with an HCMV, and previously fixed with acetone, then dried, preferably in air;

a first selection of those of the clones which give rise to fixation reaction, detectable by immunofluorescence, is carried out on said human cells after fixation of the latter with acetone and when appropriate, a second selection of those of the monoclonal antibodies retained at the end of the first selection is carried out, which antibodies react selectively with a viral protein currently induced in the nuclei of said infected cells, and which diffuse then into the cellular cytoplasm, from which it can, as the case may be, be separated, this protein having a molecular weight of the order of 68,000, this protein possessing in addition, a protein-kinase activity and the antibody selected is recovered from the reaction product obtained.

The recovery of the monoclonal antibody can be carried out in any manner known in itself, for example by prior complexation of the reaction product formed with a protein A, particularly *Staphylococcus aureus*, by dissociation of the complex form in a suitable ionic buffer.

The at least partial isolation of the polypeptide of molecular weight 68,000, having a protein-kinase activity, can involve a prior separation of the proteins or polypeptides, having different molecular weights, also contained in the cytoplasmic extracts, which can be obtained from the infected cells.

As regards more particularly the human cells utilisable for the production of the above-said polypeptide, recognised by the monoclonal antibodies produced by the hybridomas concerned above, it is possible to resort to any type of cell capable of supporting the replication of the HCMV. Cells whose use is advantageous, are constituted by human lung fibroblasts of the MRC-5 type.

The invention relates also to the polypeptides inducible by the HCMV's in infected cells, having a molecular weight which can reach a value of the order of 68,000, a protein-kinase activity and bearing a sequential epitope, these polypeptides being obtainable from a human cell culture, particularly human lung fibroblasts, previously infected with a HCMV culture, particularly of the strain Ad-169. This polypeptide can be isolated from the cytoplasm of the infected cells. However, the invention also relates to any polypeptide of lower molecular weight, also containing the sequential epitope recognised by the above-said monoclonal antibodies. It will be obvious to the specialist that, from the moment that the monoclonal antibody according to the invention is available, it becomes possible to envisage the isolation from the above-said polypeptide, having the above said molecular weight of about 68,000, of smaller peptide sequences containing the same antigenic determinant, by resorting to techniques known in themselves, of cutting up the intact initial peptide by enzymes capable of cleaving it at specific sites. By way of examples of such proteins, may be mentioned the enzyme of *Staphylococcus aureus* V8, alpha-chymotrypsin, (mouse submaxillary gland protease, marketed by the BOEHRINGER Company), collagenase of *Vibrio alqinoluticus chemovar iophagus*, which recognises specifically the dipeptides Gly-Pro and Gly-Ala.

It then becomes possible, from the peptides fragmented in controlled manner by means of such enzymes, to detect those which contain the antigenic sites by reaction with the monoclonal antibody, and which, as the case may be, also preserve the above-said protein-kinase activities.

Additional characteristics of the preferred polypeptides according to the invention are as follows;

they possess a protein-kinase activity of the casein-kinase II type; in particular, they are adapted to transfer phosphorus from ATP to casein, and also to other substrates, such as phosvitine, glycogen-synthetase, histones and alpha-phosphorylases.

the activity of protein-kinase is inhibited by quercitine;

this polypeptide is capable of being autophosphorylized in-vitro;

it is thermosensitive (loss of activity at −70° C. and at 100° C.).

The invention relates also more particularly to an in vitro process of diagnosis employing the above-said monoclonal antibodies, this process including the contacting of said monoclonal antibodies within the cells of which the infected character or not is sought, and the detection, preferably by immunofluorescence on the treated cells, without destruction of the latter, of the above-said polypeptide. Preferred conditions in which the test may be employed will be indicated below.

The employment of these particular monoclonal antibodies in diagnostic tests is particularly advantageous, in that it can be carried out very rapidly, as soon as there has been infection. It has in fact been seen that the induced protein appears from 3 to 5 hours after infection, and persists throughout the infectious cycle. This property distinguishes this monoclonal antibody very particularly from other monoclonal antibodies. It is particularly useful in diagnostic tests, in as much as it is true that in practice, the moment of the initiation of infection is generally unknown, especially when the tests are carried out on cells obtained from tissue biopsies, or other cell samplings in patients suspected of being carriers of an infection with cytomegaloviruses.

The monoclonal antibodies employed within the scope of the invention may also be the basis of what may be considered as a purification process of a protein or glycoprotein polypeptide, or again, of a fragment of the latter, containing a sequential antigenic determinant of HCMV and/or possessing similar protein-kinase activities, from extracts or from lysates of human cell cultures, previously infected with HCMV. In a preferred form of this process, recourse is had to monoclonal antibodies of the type of those which have been defined above, fixed previously, for example with cyanogen bromide to a solid support, such as the agarose lattice with three dimensional cross-linking, marketed under the trademark SEPHAROSE by the Swedish Company; PHARMACIA AG.

The continuous sequential character of the antigenic determinant of the polypeptides according to the invention results from the fact that the polypeptide bearing it can always be isolated from the cytoplasmic extract of infected cells, even when the separation operation is carried out in the presence of powerful detergents like sodium dodecylsulfate (SDS), sodium deoxycholate, or the detergent marketed under the trademark TRITON X-100, with or without beta-mercaptoethanol. The above-mentioned agents are in fact known for their capacity to "undo" or to "unfold" a protein. Any "conformational" antigenic determinant would then cease to be recognised by the monoclonal antibody and this especially on the hypothesis that the "conformational site" involving amino acid sequences, which happened to be in the same neighbourhood in the natural protein was only a consequence of the closeness of sequences not directly linked with one another due to the initial conformation of said protein. It results from the foregoing that the protein or polypeptide which carries said antigenic site, is apparently also immunogenic, and consequently adapted to induce the production in vivo of antibodies neutralising the virus itself.

If the antibodies according to the invention enable the detection specifically of the protein of molecular weight about 68,000 in a cell extract, as the case requires protected against enzymatic degradations, to the exclusion of any other polypeptide or protein, having distinct molecular weights, the consequence thereof is that this polypeptide or protein will itself be useable in turn to carry out the selection and isolation of monoclonal antibodies capable of being produced by hybridomas obtained by cell fusions, bringing into action initially other types of myelomas, on the one hand, and other MCMV's for the immunisation of the spleen cells intended to be fused with said myeloma cells on the other hand.

Additional characteristics of the invention will appear also in the course of the description which follows of examples of the production of hybridomas and of the isolation of those among them which are adapted to produce antibodies according to the invention.

The techniques which have been employed in the performance of these examples have been carried out according to the following operational modes:

1) Preparation of the Hybridomas

Mice were immunised by intraperitoneal injection of a suspension of infected and unfrozen human MRC-5 cells. The cells had been frozen five days after their infection with a strain of HCMV Ad-169. A booster-injection was administered to these mice 3 or 4 weeks later. The mice were sacrificed and the spleens recovered for their cell fusion 3 days after the booster injection. The spleen cells were fused with cells of myeloma $SP^2/OAg\ 14$ (SCHULMANN et coll. strain, "Nature", 1978, 276, 269/270) and the hybridomes formed were selected in an RPMI medium containing hypoxantine (5 mM) and azaserine (1 mM) according to the technique described by R. CRAINIC et Coll. "Develop. Biol. Standard.", 1982, 50, 229–234, with respect to the production of hybridomas secreting monoclonal antibodies against the virus of poliomyelitis.

2) Selection of Positive Hybridomas

The supernatant liquors of the hybridoma cultures thus retained, were selected for their capacity to secrete specific antibodies against HCMV by indirect immunofluorescence, by means of late antigen preparations. A series of positive hybridomas was cloned by the method of limited dilutions, and the supernatants of these, clones were then tested in the same manner by indirect fluorescence, by the method described in the article above mentioned of C. AMADEI et Coll. Then those of the hybridomas which secreted monoclonal antibodies having characteristics similar to those of the monoclonal antibodies F6b of C. AMADEI et Coll,. were selected. It is one of these strains which has been deposited at the C.N.C.M., under N° I-289.

3) Labeling of the Monoclonal Antibodies

The clones ($2 \times 10^6$ cells) were labeled either with $^{35}S$-methionine, or with $^3H$-methionine, also by the technique described by C AMADEI et Coll.

4) Detection of the Fixation on the Protein A

It was again carried out by the method described in the article of AMADEI et Coll.

The tests mentioned under paragraphs 3) and 4) were more particularly intended for the recognition of the ability of the monoclonal antibodies of producing a reaction detectable by immunofluorescence with human cells in cultures previously infected with HCMV, and in addition, of their capacity of being precipitated by protein A.

In order to detect among these monoclonal antibodies those which are in addition capable of only reacting with a single polypeptide of molecular weight of the order of 68,000, it is preferred to carry out a prior radioactive labeling or the like of previously infected human cells, from which the cellular extracts are subsequently recovered. It is these cellular extracts which will then be made to react with the unlabeled monoclonal antibodies to be selected.

5) Extraction of the Antigen

Cells, whether infected or not, were washed twice in situ, with a saline solution buffered with phosphate (PBS) containing calcium and magnesium ions (complete PBS), then recovered by scraping in complete PBS containing phenyl-methyl-sulfonyl fluoride $10^{-4}$ M (PMSF) and diisopropylfluoro-phosphate $10^{-4}$ (DFP), the cells being finally subjected to extraction in a solution having a high salt content and high pH containing 0.5% of the detergent marketed under the name NP-40, by the technique of MICHELSON et Coll., (1979) J. Virol. 32, 259–267. In some cases, the nuclei were separated from the cytoplasma after swelling of the cells in a hypotonic buffer, the addition of NP-40 (final concentration 0.5%) and subjection of the cell suspension to the action of a plunger piston to break the cells (by the technique of MICHELSON et Coll. The suspension was then centrifuged at 800 g for 5 minutes at 4° C. The nuclei were then retained in the pellet formed and the supernatant constituting the cytoplasmic fraction was then recovered. The nuclei were subjected to the same extraction treatment as mentioned above.

All the extracts were centrifuged at 15,000 g for 15–30 minutes at 4° C. and frozen at −70° C. until the time of use. For the tests of measurement of phosphotransferase activity, there followed the immediate immunoprecipitation of the desired antigen, under the conditions indicated below. The antigen can be preserved in the state bound to *Staphylococcus aureus*.

6) Immunoprecipitation

The precipitation were carried out by employing 5 microliters of ascites fluid per 200 micrograms of protein extracted. The antigen and the monoclonal antibodies (F6b) were incubated with stirring for 1.5 hour at ambient temperature. The protein A was added in the form of a 10% suspension of a strain of *S. aureus* stereotype 1 of Cowan, inactivated by heat and fixed with formaldehyde (50 microliters/5 microliters of ascites fluid). The antigenic antibody complexes were washed three times in NEIS medium (KESSLER S. W. (1975) J. Immunol. 115, 1617–1624), then stored in this buffer in the form of a 10% suspension at 4° C. The complex can also be dissociated in an electrophoresis buffer by heating for five minutes at 100° C. The immunoprecipitate was analysed on sodium-dodecyl-sulfate-polyacrylamide electrophoresis gel (SDS-PAGE 10%). The resolution of the proteins was carried out by differential migration with a current of 30–35 mA. When appropriate, fluorography was carried out by the method of BONNAR et Coll. (1974), Eur. J. Biochem. 46, 83–88, with the modification consisting of the use of a single bath based on dimethysulfoxide (DMSO) for 15 minutes at 37° C. and a single bath of DMSO+20% of 2,5-diphenyloxazole (PPO) for 30 minutes at 37° C.

7) Radioactive Labeling of the Cells

Infected cells were selected one hour subsequent to infection and deprived of methionine for 15 minutes. Absorption with the virus was then carried out in a medium containing 10 microcuries/milliliter of $^{35}$S-methionine. For the other specimens of infected cells, the virus was absorbed for 1 hour and a growth medium was added. All the cells were deprived of methionine for 15 minutes before being labeled for 2 hours before their sampling at the respective times of 3, 9, 24, 48, 72 and 96 hours after infection. The uninfected cells were labeled in the same mariner. The labeling medium consisted of an Eagle minimum essential medium, devoid of methionine, containing 10 microcuries/milliliter of $^{35}$S-methionine (AMERSHAM, specific activity 1300 curies/mmole). The labeling of the phosphoproteins was carried out over 3 hours in a modified Dulbecco medium, devoid of phosphate, containing 100 microcuries/milliliter of $^{32}$p-orthophosphate.

8) Demonstration of the Protein-Kinase Activity

Except when otherwise specified, the test for the protein-kinase activity was carried out by using 50 microlitres of enzyme, bound to bacteria in a medium (final volume of 100 microliters) containing magnesium phosphate buffer 22 mM at pH 6.8 KPi, magnesium sulfate $MgSO_4$ 5 mM EDTA 0.15 mM, ATP 0.1 mM, 3 microcuries of $^{32}$p-ATP, and 1 milligram per milliliter of casein. The casein was not present in the analysis tests of immunoprecipitates in the SDS-PAGE gel. The immunoprecipitates were then washed as indicated above, re-suspended in the reaction mixture, and incubated for 30 minutes at 30° C. The reaction was stopped with 10 microliters of EDTA solution 0.3 M. The immunoprecipitates were separated by centrifugation at 5000 g over 4 minutes at 4° C. The supernatants were precipitated with a 5% trichloracetic acid solution (TCA). The precipitates were dissolved in a 1 M soda solution, then reprecipitated with TCA, washed by filtration on filters marketed under the name WHATMAN G.F/C. After additional washing in ethanol, the filters were dried and the pulses counted in a PACKARD scintillator liquid. The immunoprecipitates intended for analysis on gel were washed 3 times in KPi buffer, re-suspended in the buffer of the electrophoresis and analysed in 10% SDS/PAGE gel under the above indicated conditions.

9) Estimation of the Sedimentation Coefficient

The antigen labeled with $^{35}$S-methionine was prepared and extracted as indicated above from infected cells for 120 hours. The antigen was then deposited at the upper part of a 5–25% sucrose gradient formed in PBS and subjected to centrifugation in a BECKMAN SW-41 rotor at 35,000 revolutions per minute for 17.25 hours at 4° C. Fractions were collected. Each fraction was immunoprecipitated with F6b monoclonal antibody then analysed on SDS-PAGE.

10) Electrophoresis of the Amino Acids Labeled with $^{32}$p

After the protein-kinase reaction employing precipitates obtained in the absence of caseins the product labeled with $^{32}$p is detached with a 0.1% $NH_4$ $HCO_3$ solution containing 0.1% of SDS. The sample was dried under vacuum, re-suspended in 6M, HCl and hydrolysed overnight at 110° C. After evaporation of HCl, the preparations were re-suspended in the electrophoresis buffer. The phosphoaminoacids were separated at pH 3.5, (in a medium formed from 50 milliliters of acetic acid and 5 milliliters of pyridine per liter) over 45 minutes under 1000 V on thin cellulose-coated plates (marketed by MACHEREY-NAGEL & Co). Standards were dyed with the cadmiumninhydrin reagent (described by DRICKAMER et Coll., J. Biol. Chem. (1982) 257, 15156–15161) and the plates were exposed to a Kodak X-Omat film for one week.

The polypeptide immunoprecipitated by the monoclonal antibody F6b had a molecular weight of about 68,000 (p68). It was immunoprecipitable from nuclei of infected cells, from the third hour after infection. It can be immunoprecipitated also from cytoplasmic extracts 24 hours after infection. The content of this polypeptide with respect to the whole of the extracted proteins, 96 hours after infection, reached 0.5% (evaluation on the basis of the percentage of radioactivity contained in the immunoprecipitate recovered). This polypeptide has a sedimentation coefficient in water at 20° of 6.9 (by comparison with labels consisting of catalase and of bovine albumin serum).

The molecular weight of p68 was evaluate with respect to the migration distances in the same electrophoretic system, of the following four substances of known molecular weights:

phosphorylase A (94,000);

bovine serum albumin (68,000);

fumarase (49,000);

aldolase (40,000).

The results witness the in vitro phosphorylation capacities of the polypeptide, which have been indicated above. The protein-kinase reaction with casein used as an acceptor, is done optimally at pH 6–6.5. It declines rapidly in media at more acid or more alkaline pH's. The reaction depends an the presence of $Mg^{2+}$ ions. These reactions are not cAMP-dependant. The phosphate transfer reaction is not operative in the presence of manganese at high pH. This polypeptide (or this enzyme) is stable. It can be preserved in the form of a conjugate with S. aureus, without loss of activity after storage for 6 weeks at 4° C. The complexation with F6b monoclonal antibodies does not result in loss of activity.

This enzyme can be autophosphorylated, the latter taking part at the level of aminoacyl residues constituted by threonine and serine.

Polypeptides having molecular weights of the order of 68,000 and showing the same characteristics as those which have been indicated above, are induced in infected human cells, particularly lung fibroblasts, by other strains of cytomegalovirus, particularly human strains TOWNE & DAVIS. On the other hand cytomegalovirus strains specific to the monkey (COLBURN strain and SGC strain) do not induce the production of a protein of molecular weight 68,000 recognisable by monoclonal antibodies secreted by the strain F6b.

The invention therefore relates more particularly to the selection of strains producing monoclonal antibodies having the characteristics of the F6b monoclonal antibodies.

The employment of this monoclonal antibody enables indeed efficient diagnosis in vitro of a viral infection by HCMV. It has already been indicated that this detection could be done practically at any moment of the infectious cycle, particularly by immunofluorescence reaction. This monoclonal antibody has also the great advantage that the diagnosis carried out by immunofluorescence can be confirmed, by the capacity of the same antibody to form complexes with a protein induced by human cytomegaloviruses which protein can then be detected owing to its protein-kinase activity The latter can be detected with a high level of accuracy. Finally, the use of monoclonal antibodies of the above-indicated type can be practiced in quantitative dosage tests of the level of infection of the human cells afflicted.

The invention relates also to the polypeptide itself, both as a biological reagent of great value, for example, in virus identification tests, when their classification within cytomegaloviruses does not a priori seem certain. On the contrary, it can be used for the selection of the most effective monoclonal antibodies for the constitution of diagnosis "kits".

The invention relates also to "kits" for performing in vitro diagnoses as described above. Particularly a preferred "kit" comprises:

at least one microplate, a preparation containing monoclonal antibodies suitable for the diagnosis, control cellular extracts (obtained from human cells, particularly of the human MRC-5 type, these cells having or not been previously infected with HCMV).

labeled antibodies (radioactive, enzymatic, fluorescent or other label directed against immunoglobulins of human blood, suitable buffers for the performance of the various operations and for the final examination of the products which have reacted to the fluorescence microscope.

Such an outfit will, for example, be employed in the following manner:

a cellular extract coming from a cellular biopsy to be examined is deposited in one or several cups of the titration plate and adsorbed at their surface;

into the cups or wells of the microplate are introduced doses of the monoclonal antibody preparation;

the plate is placed to incubate at a suitable temperature;

the microplate is then efficiently washed;

then there is introduced into the cups of the microplate labeled antibodies directed against blood immunoglobulins, hence against the monoclonal antibodies, and it is again incubated;

the label is detected (for example by action on the suitable substrate when the label is constituted by an enzyme), all of these operations being also carried out with respect to control cell extracts, and this for the purposes of comparison.

Advantageously, it is possible also to carry out detection tests and quantitative dosage tests, for example, by passage of a cellular extract obtained under conditions for example of the type of those which have been envisaged above, on an affinity chromatography column comprising the monoclonal antibodies fixed to agarose gel, for example, as has been indicated above, the dissociation of the complex possibly formed between the monoclonal antibodies used, and the polypeptide specifically recognised by the latter, and the quantitative dosage of the polypeptide, by employing its protein-kinase properties.

As is self-evident and as emerges already from the foregoing, the invention is in no way limited to those of its types of application and embodiments which have been more especially envisaged; it encompasses on the contrary all modifications.

What is claimed is:

1. In a process for in vitro detection of an infection of cells of a human by human cytomegalovirus, which comprises the step of contacting intact cells of said human or extracts of cells of said human with monoclonal antibodies which react with polypeptides produced by said cells when infected by human cytomegalovirus, the improvement in said process which comprises:

a) said monoclonal antibodies reacting with said cells and being detectable when said cells have previously been
i) infected with human cytomegalovirus and ii) cultured; and b) said monoclonal antibodies reacting selectively with a single polypeptide in said cells to form a complex with said polypeptide; said polypeptide having a molecular weight of about 68,000 and being recognized by the monoclonal antibody produced in the hybridoma deposited in the C.N.C.M. (National Collection of Microorganisms and Cultures) under accession No. I-289; said polypeptide being present in the nuclei of said cells and diffusing from said nuclei into the cytoplasm of said cells when said cells are infected by human cytomegalovirus; said polypeptide which is inducible in human cells by human cytornegalovirus persisting throughout the infectious cycle; said polypeptide possessing a protein-kinase activity; and said polypeptide being a viral polypeptide induced in the nuclei of cells infected by human cytomegalovirus.

2. The process of claim 1, wherein said monoclonal antibodies have the additional property of being able to react with protein A.

3. The process of claim 2, wherein said monoclonal antibodies are murine monoclonal antibodies.

4. The process of claim 1, wherein said monoclonal antibodies give rise to reactions detectable by immunofluorescence when said cells are fixed with acetone.

5. The process of claim 1, wherein after said cells are contacted with said monoclonal antibodies to from said complex with said polypeptide, said polypeptide is extracted from said complex; said extracted polypeptide is then immunoprecipitated; and the protein-kinase activity of said immunoprecipitated polypeptide is then measured.

6. The process according to claim 1 further comprising the step of after culturing said intact cells in step (a) (ii), the intact cells are then fixed with acetone.

7. A kit for in vitro detection of human cells infected by human cytomegalovirus, which comprises:
 a) monoclonal antibodies which:
  (1) react with said infected cell and being detectable when said cells have previously been cultured; and
  (2) react selectively with a single polypeptide, in said infected cells to form a complex with said polypeptide, said polypeptide (i) having a molecular weight of about 68,000 (ii) being recognized by the monoclonal antibody produced in the hybridoma deposited in the C.N.C.M. (National Collection of Microorganisms and Cultures) under accession No. I-289; (iii) being present in the nuclei of said infected cells and diffusing from said nuclei into the cytoplasm of said infected cells; (iv) possessing a protein-kinase activity; (v) being inducible in human cells by human cytomegalovirus persisting throughout the infectious cycle; and (vi) being a viral polypeptide induced in the nuclei of cells infected by human cytomegalovirus;
 b) control cells free of infection by human cytomegalovirus or extracts of said control cells;
 c) labeled antibodies directed against immunoglobulins of human blood capable of recognizing said monoclonal antibodies; and
 d) buffers suitable for enabling the formation a complex between:
  (1) cells infected by human cytomegalovirus or extracts of said infected cells; and
  (2) said monoclonal antibodies.

8. The kit according to claim 7, wherein said monoclonal antibodies which give rise to reactions with said infected cells, after being cultured in (1), are further fixed with acetone.

* * * * *